United States Patent [19]

Müller et al.

[11] Patent Number: 5,075,447
[45] Date of Patent: Dec. 24, 1991

[54] RUTHENIUM COMPLEXES USEFUL AS CARRIERS FOR IMMUNOLOGICALLY ACTIVE MATERIALS

[75] Inventors: Francis Müller; Dieter Schmidt, both of Basle, Switzerland

[73] Assignee: Hoffmann-La Roche Inc., Nutley, N.J.

[21] Appl. No.: 153,128

[22] Filed: Feb. 8, 1988

Related U.S. Application Data

[62] Division of Ser. No. 773,956, Sep. 9, 1985, Pat. No. 4,745,076.

[51] Int. Cl.[5] ............................................. C07F 15/00
[52] U.S. Cl. ...................................................... 546/10
[58] Field of Search .......................................... 546/10

[56] References Cited

U.S. PATENT DOCUMENTS 4,205,952  6/1980  Cais .
4,283,382  8/1981  Frank et al. .
4,293,310 10/1981  Weber .
4,341,757  7/1982  Spallholz .
4,372,745  2/1983  Mandle et al. .
4,374,120  2/1983  Soini et al. .
4,587,223  5/1986  Soini et al. .

OTHER PUBLICATIONS

JACS, 95: 3158–3162 (1973).
JACS, 98: 6536–6544 (1976).
J. Org. Chem., 27: 865–868 (1962).
J. Org. Chem. 27: 1641–1643 (1962).
J. Org. Chem. 75: 1541–1545 (1951).
Helvetica Chimica, pp. 1675–1702 (1980).
Chemical Abstracts, 98: 118503t (1983).
Chemical Abstracts, 94: 216784y (1981).
Aust. J. Chem., 17: 325–336 (1964).
J. Inorg. Nucl. Chem., 41: 495–502 (1979).

Primary Examiner—Robert A. Wax
Assistant Examiner—Frederick F. Tsung
Attorney, Agent, or Firm—George M. Gould; George W. Johnston; Alan P. Kass

[57] ABSTRACT

The invention relates to a ruthenium complex having the formula $$Ru^{2+}L_1L_2L_3 \qquad \qquad I$$

wherein $L_1$, $L_2$ and $L_3$ are the same or different are equal to a bi- or polycyclic ligand with at least two nitrogen-containing heterocycles, whereby at least one of these ligands is substituted with at least one group conferring water-solubility, and whereby at least one of these ligands is substituted, optionally via a spacer group, with at least one reactive group, and whereby the ligands $L_1$, $L_2$ and $L_3$ are attached to the ruthenium via nitrogen atoms.

The invention is further related to such ruthenium complexes having coupled thereto an immunologically active material, for example, antigens, haptens or antibodies and to the use of said ruthenium complexes in fluorescence spectroscopy. Specific ligands $L_1$, $L_2$ and $L_3$ which are useful in the ruthenium complexes of the invention are, e.g., 2,2'-bipyridine, 1,10-phenanthroline benzbathophenanthroline or bathophenanthroline groups. Groups which are useful for conferring water-solubility on said ligand are, e.g. sulfonic acid groups which are preferably present in the form of their salts. Useful spacer groups are e.g. an alkylene group containing 1–8 carbon atoms and which is optionally substituted with $-SO_2-NH-$, $-S-$, $-O-$, $-COO-$ or $-CO-NH-$ groups. Useful reactive groups to which the immunologically active material is coupled, are e.g. $-COOH$, $-I$, $-NH_2$, $-NCS$ or $-SO_2Hal$ groups. The ruthenium complexes according to the present invention can be detected with great sensitivity by fluorescence spectroscopy and are thus useful in fluorescence immunoassays.

4 Claims, No Drawings

RUTHENIUM COMPLEXES USEFUL AS CARRIERS FOR IMMUNOLOGICALLY ACTIVE MATERIALS

This is a division, of application Ser. No. 773,956 filed Sept. 9, 1985, now U.S. Pat. No. 4,745,076.

The present invention is directed to ruthenium complexes to which can be coupled an immunologically active material. The ruthenium complexes of the invention have the general formula $$Ru^{2+}L_1L_2L_3 \qquad \text{I}$$

wherein $L_1$, $L_2$ and $L_3$ are the same or different and are equal to a bi- or polycyclic ligand with at least two nitrogen-containing heterocycles, whereby at least one of the ligands $L_1$, $L_2$ or $L_3$ is substituted with at least one group conferring water-solubility. and whereby at least one of these ligands is substituted optionally via a spacer group, with at least one reactive group, and whereby the ligands $L_1$, $L_2$ and $L_3$ are attached to the ruthenium via nitrogen atoms.

The ligands $L_1$ and $L_2$ can be the same or different and are equal to, for example, 2,2'-bipyridine, 1,10-phenanthroline, benzbathcpbenanthroline or especially bathophenanthrolene groups. The ligands $L_1$ and $L_2$ are preferably the same.

The ligand L is equal to, for example, a 2,2'-bi-pyridine, 1,10-phenanthroline or especially a bathophenanthroline group.

In the ruthenium complexes of the invention, groups which are useful for conferring water-solubility on the ligands $L_1$ and $L_2$ are sulphonic acid groups which are preferably present in the form of their satls. The sodium salts are especially preferred.

As used herein, the term "spacer group" refers to an alkylene group having a maximum of 8 carbon atoms, which optionally can contain —SO₂—NH—, —S—, —O—, —COO— or —CO—NH— functionalities.

As used herein, the term "reactive group(s)" refers to the group to which is coupled the immunologically active material suitable "reactive groups" are for example, —COOH, —I—, —NH₂, —NCS or —SO₂Halogen groups.

As used herein 2,2'-bipyridine (bpy) refers to a compound of the formula:

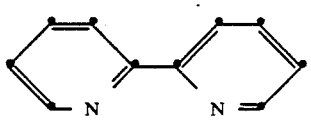

1,10-phenanthroline refers to a compound of the formula:

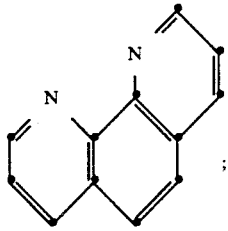

bathophenanthroline (batho) refers to a compound of the formula:

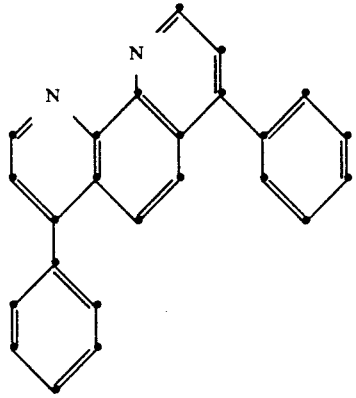

and benzobathophencenthroline (benzobatho) refers to a compound of the formula

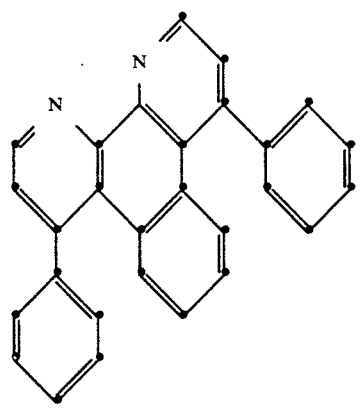

In the case of Ru complexes having 3 identical ligands $L_1$, $L_2$ and $L_3$ the ligand must have not only a gorup conferring water-solubility, but also a spacer group with a reactive group.

A ligand suitable for this purpose is the compound of the formula

[(SO₃Na)(SO₂NHCH₂CH₂COOH)batho], i.e.,

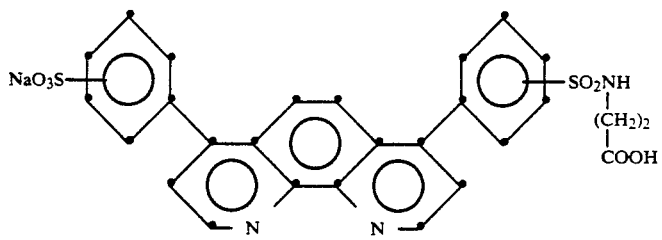

In the case of Ru complexes which have two different ligand types, one ligand type can carry the group or groups conferring water-solubility, while the other ligand can substituted by one or more linking groups, i.e., a reactive group which is attached to the heterocycle via a spacer group.

Preferred for use herein are ruthenium complexes wherein $L_1$ and $L_2$ are the same and which have the formula

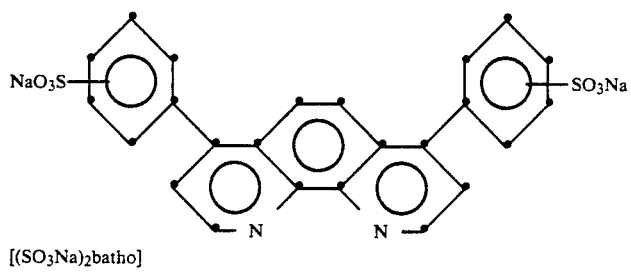

[$(SO_3Na)_2$batho]

and wherein the ligand $L_3$ is preferably selected from the following group:

[$(SO_3Na)_2$batho]

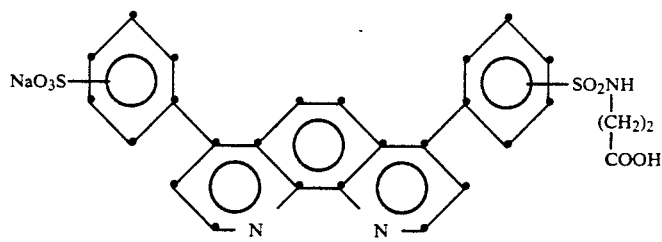

[$(SO_2NHCH_2COOH)_2$batho]

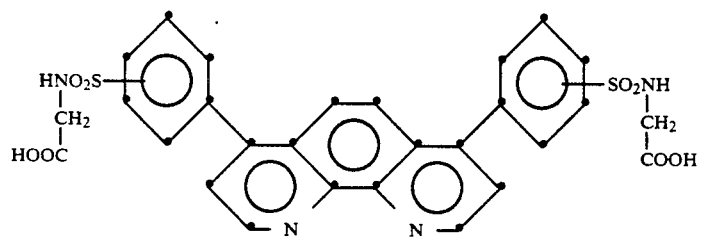

[$(SO_2NHCH_2CH_2COOH)_2$batho]

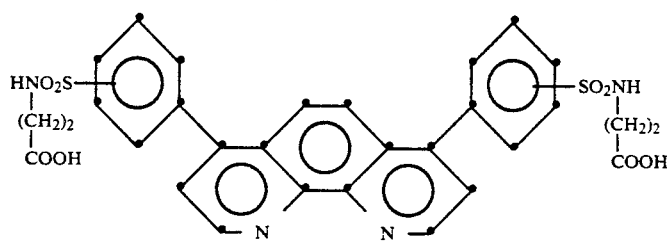

[$(SO_2NHCH_2CH_2CH_2COOH)_2$batho]

-continued

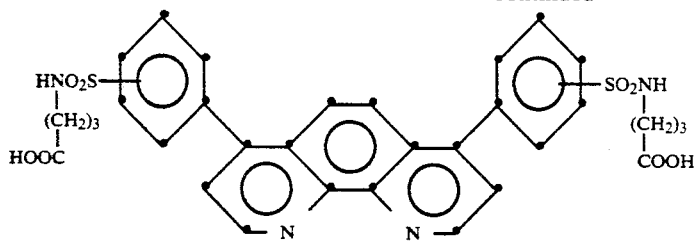

[(SO₂NHCH₂CH₂CH₂CH₂CH₂COOH)batho]

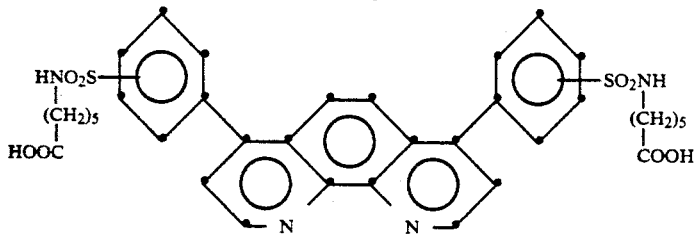

[(CH₂CH₂CH₂CH₂COOH)batho]

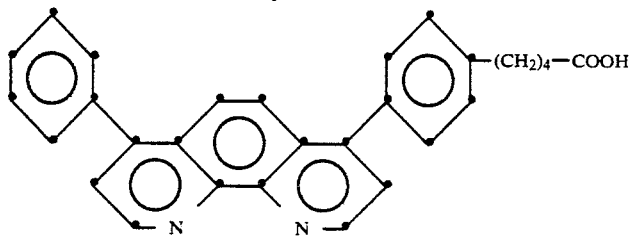

[(CH₂CH₂CH₂CH₂CH₂COOH)batho]

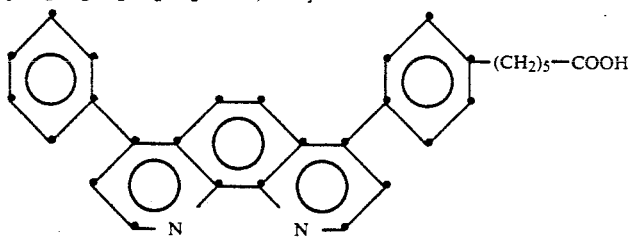

[(CH₂CH₂CH₂COOH)benzobatho]

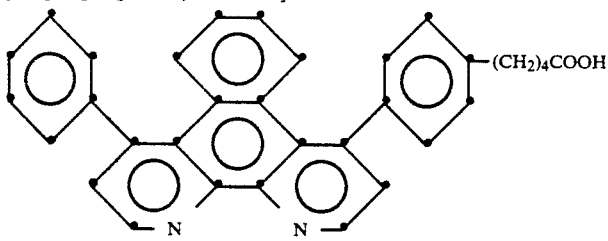

[(COOH)₂bpy]

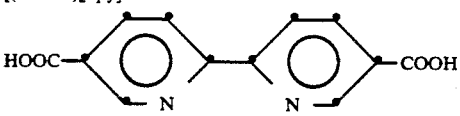

The synthesis of the ligand $L_3$, carrying the linking group or grups, is carried out according to processes which are described schematically hereinafter:

(1) Preparation of [(SO₂NH(CH₂) x COO—t-butyl)$_x$-batho] and [(SO₃Na)(SO₂NHCH₂CH₂ COO—t-butyl)]batho.

Briefly, the synthesis of the ligand $L_3$, which carries the linking group or groups, is carried out using the disodium salt of the bathophenanthroline disulphonic acid as the starting material. From this there is firstly prepared with PCl₅ the corresponding disulphochloride (see F. Muth in "Houben-Weyl, Methoden der Organischen Chemie", vol IX, p. 563, 4th edition 1955, G. Thieme Verlag, Stuttgart). This is subsequently converted into the corresponding sulphonamide with the t-butyl ester of an amino acid (such as e.g. β-alanine, glycine, 4-amino- butyric acid or 6-aminocaproic acid) in accordance with the following Scheme (see F. Muth in ∂Houben-Weyl, Methoden der Organischen Chemie", vol IX, p. 609, 4th edition 1955, G. Theime Verlag Stuttgart):

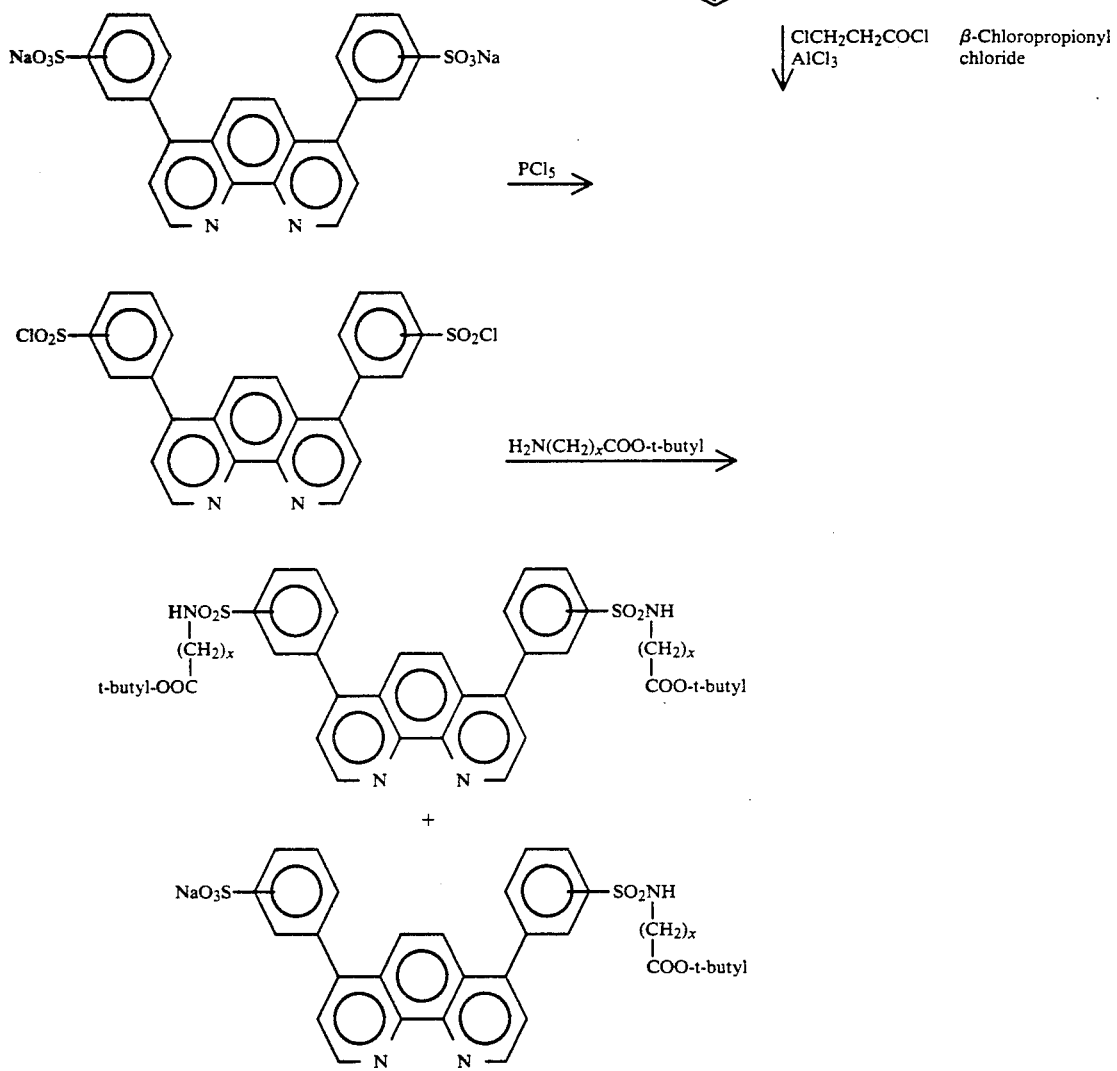

In the above reaction in addition to the disulphonamide there is also obtained the monosulphonamide as a byproduct. The saponification of the t-butyl ester is carried only after the synthesis of the corresponding Ru complex.

(b) Preparation of [CH$_2$CH$_2$CH$_2$CH$_2$COOH)batho] or [(CH$_2$CH$_2$CH$_2$CH$_2$CH$_2$COOH)batho]

The synthesis of L$_3$ ligands having valeric acid or caproic acid as the linking group is carried out by means of a Skraup's reaction (see F. H. Case and P. F. Strohm; J. Org. Chem. 27, 1641 (1962)) from 4-phenyl-8-amino-quinoline (see F. H. Case; J. Org. Chem. 16, 1541 (1951)) and the p-[β-chloropropionyl] derivatives of the corresponding 1-phenyl fatty acid methyl esters, whereby the latter are obtained by acylating methyl 5-phenylvalerate (Fluka) or methyl 6-phenylcaproate (see W. E. Truce and C. E. Olson: J. Amer. Chem. Soc. 75, 1651 (1953)) with β-chloropropionyl chloride, in accordance with the following Scheme:

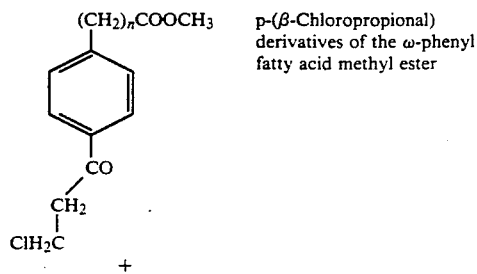

-continued
Reaction Scheme

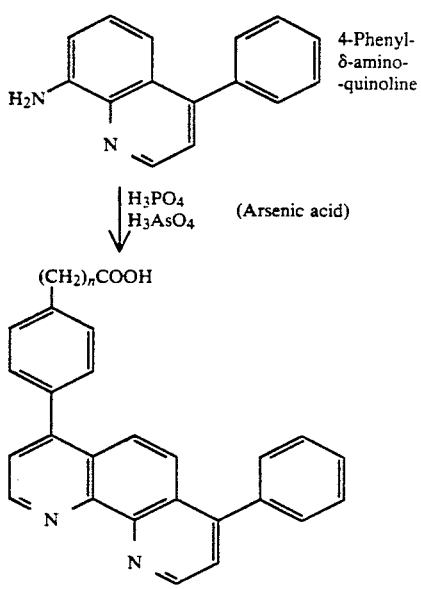

4-Phenyl-δ-amino-quinoline

↓ H₃PO₄, H₃AsO₄ (Arsenic acid)

$(CH_2)_n COOH$

5-[p-(7-Phenyl-1,10-phenanthrolin-4-yl)phenyl]
pentanoic acid = {(CH₂CH₂CH₂CH₂COOH)batho}
6-[p-(7-Phenyl-1,10-phenanthrolin-4-yl)phenyl]
hexanoic acid = {(CH₂CH₂CH₂CH₂CH₂COOH)batho}

(c) Preparation of [(CH₂CH₂CH₂CH₂COOH) benzobatho],

The synthesis of this benzo-bathophenanthrolinepentanoic acid, is carried out via several steps from 2-amino-3-naphthoic acid in accordance with the following Scheme (see E. Koft and F. H. Case; J. Org. Chem. 27, 865 (1962)).

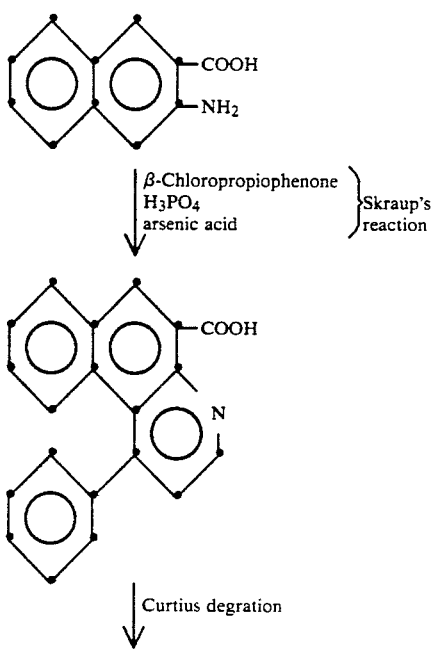

↓ Curtius degration

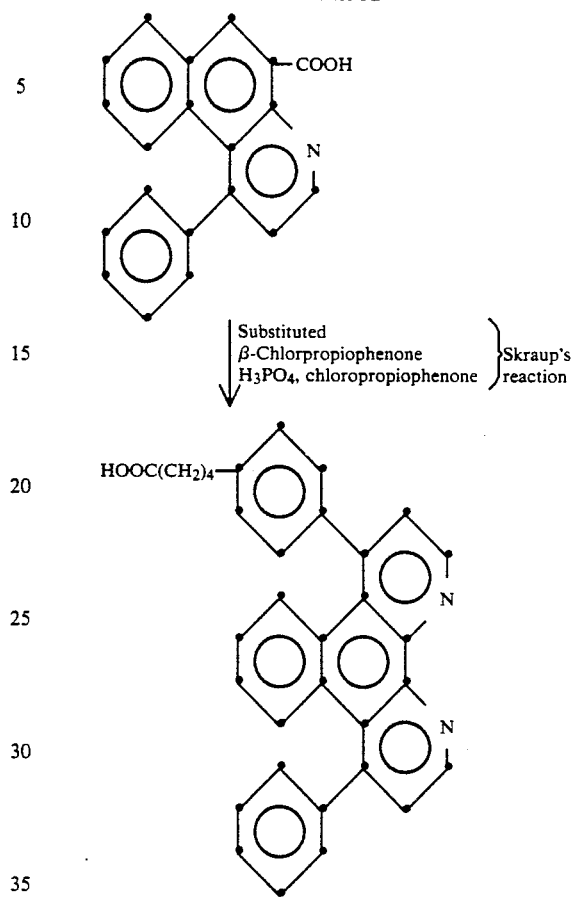

↓ Substituted β-Chlorpropiophenone, H₃PO₄, chloropropiophenone } Skraup's reaction The synthesis of Ru complexes wherein L₁, L₂ and L₃ ligands are identical to each other can be carried out according to either of two processes described in the literature.

According to Braddock and Meyer (J. Am. Chem. Soc. 95, 3158 (1973)] water-soluble ruthenium tricnloride is heated togethez with the ligands for an extended period of time in DMF whereby the complex is formed with partial decomposition of the solvent.

However, the process described by Lin et al. [J. Am. Chem. Soc. 98, 6536 (1976)] is preferably used. In this process potassium pentachloroaquoruthenate (K₂Ru Cl₅·H₂O) is heated in a weak hydrochloric acid environment with a 3-fold stoichiometric amount of ligand and the solution is subsequently reduced with sodium hypophosphite.

The synthesis of ruthenium complexes having 2 different ligand types is carried out according to known procedure, e.g. in accordance with Belser et al. Helv. Chim. Acta 63, 1675 (1980).

When the ligand L is different from the ligands L₁ and L₂ a stepwise synthesis of the complex is preferred. (As would be recognized by one skilled in the art, the complex can also be prepared by means of a statistical synthesis, but this route is not preferred, as it is difficult to control.) Thus, there is prepared in a first step with water-soluble ruthenium trichloride and double the stoichiometric amount of ligand L₁ or L₂ in dimethylformamide (with lithium chloride as the catalyst) the intermediate RuL₁L₂Cl₂. This intermediate is subsequently converted into the desired mixed complex with the ligand L₃.

If there is used as the ligand L₃ a compound whose reactive group is present in protected form—e.g. as the t-butyl ester in the case of the sulphonamide derivatives of bathophenanthroline—then the cleavage of this protecting group is preferably carried out only after the synthesis of the corresponding Ru complex The isolation and purification of the ruthenium complexes formed is carried out according to conventional methods by reprecipitation column chromatography or preparative thick-layer chromatography.

Immunologically active materials, which are coupled to the ruthenium complexes of the invention which are for example, antigens haptens or antibodies (inclusive e.g. Fab fragments). Not only polyclonal antibodies, but also monoclonal antibodies can be used herein.

An especially preferred immunologically active material is an antibody against carcinoembryonal antigen. A further especially preferred immunologically active material is an antibody against human choriongonadotropin. as well as an antibody against a-interferon.

The coupling of the immunological material to the ruthenium complex is carried out in a manner known per se. A preferred coupling method comprises treating the ruthenium complex and the immunologically active material with a water-soluble carbodiimide derivative e.g. with N-cyclohexyl-N'-(2-morpholinoethyl)-carbodiimide-methyl-p-toluenesulphonate.

The ruthenium complexes of the invention can be detected very sensitively by fluorescence spectroscopy. They are very well suited as label molecules for highly sensitive fluorescence immunoassays and they are especially suitable for a time-resolved fluorescence immunoassay as is described for example. in DT-OS 26 28 158. By using the ruthenium complexes in accordance with the present invention in place of the frequently used FITC (fluorescein isothiocyanate) the detection sensitivity in the case of fluorescence immunoassays can be improved. This is of advantage especially in the determination of small amounts of antigens in body fluids such as e.g. plasma and serum. Example of such antigens are e.g. carcinoembryonal antigen (CEA), β-HCG or a-interferon.

The time-resolved fluorescence measurement is made using a measurement apparatus. Briefly the apparatus works as follows. A pulsating light source. i.e. a colour laser—excites the measurement sample to fluoresce with flashes of light of suitable wavelength. i.e. g=453 nm, whereby the duration of flash (t=0.7 ns) is much shorter than the decay time of the fluorescing label. The fluorescent radiation is then directed with an optic through an edge filter (Balzers 610). which transmits the emission wavelength of the label, to the photocathode of a photomultiplier. The individually detected photons generate pulses of current which after amplification and standardization. are counted digitally (photon counting method). By means of a photodiode the exciting flash of light simultaneously controls a gate circuit which starts the counter after an adjustable time delay (w=2 us) and which again stops the counting process after an adjustable opening time of the measurement aperture (Wt=3 μs). The time delay (W) is chosen so that during said time delay stray light effects as well the background fluorescence have died away almost completely. In this manner the number of counted pulses is proportional to the intensity of the fluorescence of the label which is measured separately from the background.

EXAMPLE 1

Preparation of Bathophenanthroline Disulphochloride 2.2 g of dry bathophenanthroline disulphonic acid disodium salt (Fluka) are mixed well with 3.1 g of $PCl_5$ and 750 μl of POCl in a 500 ml round flask. The flask, provided with a reflux condenser and a calcium chloride tube, is heated to 110° C. in an oil bath for 2.5 hours. Sublimed $PCl_5$ which has precipitated on the cooler parts of the flask is scratched off periodically. Thereafter the unreacted $PCl_5$ as well as the $POCl_3$ are removed completely at 110° C. in a water-jet vacuum within 5 hours. After cooling to room tempecature the crude sulphochloride is treated for a short time with 150 ml of benzene which are discarded (in order to remove traces of impurities). The crude sulphochloride is thereafter mixed with 150 ml of chloroform and stirred at room temperature for 1 hour. The chloroform is removed and the procedure repeated. The combined chloroform extracts are concentrated in vacuo. The sulphochloride which remains behind is then dried at 110° C. in vacuo for 4 hours (yield: 1.8 g).

EXAMPLE 2

Preparation of sulphonamide derivatives of bathophenanthroline with the t-butyl ester of β-alanine [($SO_2$—NH—$CH_2CH_2$—COO—t-butyl)2batho] and [($SO_3Na$)($SO_2NH$ $CH_2CH_2COO$—t-butyl)batho]

1.32 g of β-alanine t-butyl ester and 10.5 ml of triethylamine are dissolved in 50 ml of chloroform. To this solution are added. While stirring vigorously within 10 minutes, 2.0 g of solid bathophenanthroline disulphochloride. After stirring at room temperature for 5 hours the reaction mixture is left to stand in the dark for 4 days. Subsequently, the solvent as well as the triethylamine are removed at 40°-50° C. in vacuo. In order to completely remove the triethylamine, the residue is treated with 200 ml of chloroform which is thereafter removed in vacuo. This procedure is carried out a total of five times until the product no longer has an odour of triethylamine. The purification of the residue is carried out by chromatography over $SiO_2$ and leads to two products.

(a) Isolation of the disulphonamide [($SO_2NHCH_2CH_2COO$—t-butyl)₂batho]

The practically pure disulphonamide (Yield: 900 mg) is first eluted from the column using 8 l of acetone (b) Isolation of the monosulphonamide

[($SO_3Na$)$SO_2NH$—$CH_2CH_2$—COO—t-butyl)batho]

Using 3 l of a mixture of chloroform/methanol/water (7/3/0.5) there is eluted a further zone which on the basis of its fluorescence properties is identified by NMR as the monosulphonamide of bathophenanthroline disulphonic acid (yield: 1.2 g of crude product). The crude monosulfonamide product is further purified by dissolving it in 150 ml of chloroform. The resulting solution is shaken a total of three times with 100 ml of water each time. Thereafter the monosulphonamide is reprecipitated twice by dissolving the compound in 50 ml of methanol/chloroform (3/1) and precipitating it by the slow dropwise addition of 200 ml of ether. (Yield: 360 mg).

EXAMPLE 3

Preparation of Ru complex —Ru[(SO$_3$Na)(SO$_2$NH CH$_2$CH$_2$COOH)batho]$_3$(PF$_6$)$_2$ 18.7 mg of potassium pentachlocoaquoruthenate (K$_2$RuCl$_5$.H$_2$O) are dissolved at 60° C. in 2 ml of water to which has previously been added 1 drop of 6N HCl. To this solution are added a 3-fold stoichiometric amount of ligand (95.8 mg of the tert-butyl ester of the monosulphonamide of Example 2 dissolved in 1 ml of DMF) and the mixture is heated to reflux under nitrogen for 2.5 hours. After cooling the reaction solution the resulting Ru$^{3+}$ complex is reduced with 250µl of a 1 molar NaH$_2$O$_2$ solution to the corresponding Ru$^{2+}$ complex and then boiled at reflux for a further 2 hours. The solution is subsequently filtered treated with 900 µl of a 10% aqueous ammonium hexafluorophosphate solution and left to stand at 4° C. overnight whereupon the complex thereby precipitates. After suction filtration the complex is purified by means of preparative thick-layer chromatography (4 silica gel plates, elution agent CH$_2$Cl$_2$/MeOH/H$_2$O (7:3;0.5). A red zone in the front is isolated (50 mg of pure product) and, for saponification, is treated with 5 ml of trifluoroacetic acid at room temperature After 1 hour the trifluoroacetic acid is removed in a water-jet vacuum to give the Ru complex. Ru [(SO$_3$Na)(SO$_2$NHCH$_2$CH$_2$COOH)batho]$_3$ (PF$_6$)$_2$

EXAMPLE 4

Preparation of Ru [SO$_3$Na)$_2$batho]$_2$Cl$_2$ 627 mg of RuCl$_3$.3H$_2$O, 568 mg of LiCl and 2.36 g of bathophenanthroline disulphonic acid diMa salt (Fluka) are boiled at reflux in 8 ml of DMF for 6 hours. After cooling to room temperature the reaction solution is treated slowly with 60 ml of acetone and then left to stand at 4° C. for 20 hours. There thereby precipitates the violet crude product. This is filtered off under suction and washed well with acetone. A first purification is then carried out by reprecipitation. For this purpose. the crude product is dissolved in 50 ml of methanol and subsequently again precipitated with 500 ml of acetone/ether (1/1). This procedure is repeated. The further purification is carried out by chromatography over SiO$_2$. With 5 l of chloroform/methanol/acetone (4/3/3) there are eluted 600 mg of practically pure product (yield: 600 mg).

EXAMPLE 5

Preparation of the mixed complex-Ru [(SO$_3$Na$_2$ batho]$_2$ [(SO$_2$—NH—CH$_2$—CH$_2$—COO—t-butyl)$_2$batho]—Cl$_2$ The Ru derivative of Example 4 (76.2 mg) is dissolved in a mixture of 1 ml of water and 4 ml of methanol and mixed with 41.0 mg of the disulphonamide of Example 2 (dissolved in 3 ml of chloroform). This reaction mixture is heated at reflux under nitrogen for 3 hours whereby an orange-red solution results. Subsequently, the solvent is distilled ott to about 90% by blowing in N$_2$ and warming slightly. Upon cooling to room temperature a portion of the product precipitates out. For purification, the product is dissolved in 1.5 ml of methanol and 0.5 ml of DMF and chromatographed over SiO$_2$ with the elution agent chloroform/methanol/water (7:3:0.5) (yield: 75 mg).

EXAMPLE 6

Preparation of the Ru complex-Ru[SO$_3$Na)$_2$batho]$_2$ [(SO$_2$—NH—CH$_2$—CH$_2$—COOH)$_2$batho]Cl$_2$ The t-butyl ester of Example 5 is saponified as follows; Ru((SO$_2$Na)$_2$batho]$_2$ [(SO$_2$-NH—CH$_2$—CH$_2$—COO—t-butyl)$_2$batho]Cl$_2$ (55 mg) is dissolved in 5 ml of trifluoroacetic acid The reaction mixture is left to stand at room temperature for 1 hour and the trifluoroacetic acid is then removed at 40° C. in a water-jet vacuum. The crude product is firstly purified by column chromatography over SiO$_2$ using the following Elution agents:

300 ml of chloroform/acetone/methanol (4:3:3)
500 ml of chloroform/methanol/water (50:50:2)
500 ml of chloroform/methanol/water (50:50:5)
250 ml of chloroform/methanol/water (50:50:10)
100 ml of methanol/water (10/1)
100 ml of methanol/water (1/1).

The final purification is carried out by means of preparative thick-layer chromatography. For this purpose, 40 mg of the Ru complex are dissolved in 700 ml of water and applied to 4 PSC plates (SiO$_2$ plates from Merck). These are dried at 60° C. overnight and subsequently chromatographed with the elution agent chloroform/methanol/water (50:50:2). The main zone is scratched off and extracted three times with 40 ml of water each time (the silica gel is separated by centrifugation). After concentration final traces of SiO$_2$ are removed from the product by dissolving it in a small amount of methanol and centrifuging off the undissolved silica gel (yield: 38 mg).

EXAMPLE 7

Preparation of the bathophenanthroline disulphonamide with the t-butyl ester of glycine—[(SO$_2$NH CH$_2$—COO—t-butyl)$_2$ batho]

The above-identified sulphonamide was prepared according to the procedure of Example 1 and Example 2 using 10.3g of glycine-t-butyl ester dibenzenesulphimide salt 28 ml of triethylamine and 4.2g of bathophenanthroline disulphochloride. (Yield: 4.9 g).

EXAMPLE 8

Preparation of the mixed complex Ru[(SO$_3$Na)$_2$batho]$_2$ [(SO$_2$NH CH$_2$COO—t-butyl)$_2$batho]Cl$_2$ 3.6 g of Ru[(SO$_3$Na)$_2$batho]Cl$_2$ are dissolved in a mixture of 160 ml of methanol and 100 ml of water and mixed with 2.01 g of [(SO$_2$NH—CH$_2$COO—t-butyl)-$_2$batho] (dissolved in 80 ml of methanol). The reaction mixture is boiled at reflux under N$_2$ for 5 hours, whereby a deep red solution results. After cooling the reaction solution is concentrated in vacuo to about 70 ml and the mixed Ru complex is then precipitated by the slow dropwise addition of 1.4 l of acetone. For further purification the suction filtered crude product is reprecipitated twice. For this purpose. the precipitate is dissolved in about 150 ml of MeOH/H$_2$O/CH$_2$Cl$_2$ (2:1:0.3) and the complex is then again precipitated by the slow dropwise addition of 1.5 l of acetone.

Thereafter the product is chromatographed twice over silica gel with the elution agent CH$_2$Cl$_2$/ MeOH/-H$_2$O (7:3:0.5). After a further reprecipitation in a manner analogous to that described above there is obtained a pure product. 3.0 g of a red powder identified as the title compound.

EXAMPLE 9

Saponification of the t-butyl ester of Example 8 to Ru[So$_3$Na)$_2$batho]$_2$[(SO$_2$NH CH$_2$COOH)$_2$batho]Cl$_2$ Ru[So$_3$Na)$_2$batho]$_2$[(SO$_2$NH CH$_2$COO—t-butyl)$_2$ batho] Cl$_2$, (500 mg) is dispersed in 40 ml of trifluoroacetic acid. After stirring at room temperature for 2.5 hours the trifluoroacetic acid is removed in vacuo. The residue is dissolved in a mixture 1 ml of DMF and 3 ml of water. The complex is again precipitated from the solution by the slow dropwise addition of 500 ml of acetone/MeOH (8:2). The reprecipitation procedure is repeated twice and the resulting red powder is then dried at 70° C. in vacuo to yield 420 mg of the title compound.

EXAMPLE 10

Preparation of the bathophenanthroline disulphonamide with the t-butyl ester of 4-aminobutyric acid—[(SO$_2$NHCH$_2$CH$_2$CH$_2$COO—t-butyl)$_2$batho]

The disulphonamide was prepared in an analogous manner to that described in Example 1 and Example 2 except that 1.57g of 4-aminobutyric acid t-butyl ester. 17 ml of triethylamine and 2.1 g of bathophenanthroline disulphochloride was used. Yield: 1.3 g of ((SO$_2$N-H—CH$_2$CH$_2$ CH$_2$COO—t-butyl)2batho].

EXAMPLE 11

Preparation of the Mixed Complex-Ru[(SO$_3$Na)$_2$batho]$_2$-[(SO$_2$NHCH$_2$CH$_2$CH$_2$COO—t-butyl)$_2$batho]Cl$_2$ In an analogous manner as the procedure of Example 8. except that 1.28 g of Ru[(SO$_3$Na)$_2$batho]$_2$Cl$_2$; and 0.775 g of ((SO$_2$NH CH$_2$CH$_2$CH$_2$COO-t-butyl)$_2$batho] was used, the title compound was prepared Yield: 1.65 g of a red powder.

EXAMPLE 12

Preparation of Ru[(SO$_3$Na)$_2$batho]$_2$[(SO$_2$NHCH$_2$CH$_2$CH$_2$COOH)$_2$batho]Cl$_2$ The t-butyl ester of Example 11 (70 mg) was saponified according to the procedure of Example 9 to yield 50 mg of the corresponding acid identified as Ru[(SO$_3$-Na)$_2$ batho][(SO$_2$NHCH$_2$CH$_2$CH$_2$COOH)$_2$batho]Cl$_2$.

EXAMPLE 13

Preparation of the bathophenanthroline disulfphonamide with t-butyl ester of 6-aminocaproic acid—(SO$_2$NHCH$_2$CH$_2$ CH$_2$CH$_2$CH$_2$COO—t-butyl)$_2$batho]

In a manner analogous to the procedure described in Example 1 and Example 2 except that 2.27 g of 6-aminocaproic acid and 2.1 g of bathophenanthroline disulphochloride is used the title compound is prepared. Yield: 1.8 g of [(SO$_2$NHCH$_2$CH$_2$CH$_2$CH$_2$CH$_2$COO—t-butyl)$_2$batho].

EXAMPLE 14

Preparation of the mixed complex Ru[SO$_3$Na)$_2$-bath]$_2$ [(SO$_2$NHCH$_2$CH$_2$CH$_2$CH$_2$CH$_2$COO—t-butyl)$_2$batho[Cl$_2$ Utilizing a similar procedure as that described in Example 8, except that 2.2 g of Ru[(SO$_3$Na)$_2$batho]$_2$ Cl$_2$ and 1.49 g of [(SO$_2$NHCH$_2$CH$_2$CH$_2$CH$_2$CH$_2$COO—t-butyl)$_2$batho was used the mixed complex of the title was prepared, Yield: 2.8 g of a red powder.

EXAMPLE 15

Saponification of the t-butyl ester of Example 14 to Ru [(SO$_2$NHCH$_2$CH$_2$CH$_2$CH$_2$CH$_2$COO—t-butyl)$_2$batho[Cl$_2$ Utilizing the procedure of Example 9, 100 mg of the t-butyl ester of Example 14 was saponified to yield the title compound Yield: 85 mg

EXAMPLE 16

Preparation of Ru[(SO$_3$Na)$_2$batho]$_2$[(SO$_3$Na)(SO$_2$NH CH$_2$CH$_2$COO—t-butyl)batho]Cl$_2$ In an analogous manner as the procedure of Example 8 102 mg of Ru[(SO$_3$Na)$_2$batho]Cl$_2$ and 51 mg of [(SO$_3$-Na)(SO$_2$NH CH$_2$CH$_2$COO—t-butyl)batho] were reacted to y.ield 105 mg of a red powder identified as Ru[(SO$_3$Na)$_2$batho]$_2$[(SO$_3$Na)(SO$_2$NHCH$_2$CH$_2$COO—t-butyl)batho]Cl$_2$

EXAMPLE 17

Preparation of Ru[(SO$_3$Na)$_2$batho]$_2$[(SO$_3$Na) (SO$_2$NHCH$_2$CH$_2$COOH)batho]Cl$_2$ The t-butyl ester derivative of example 16 (105 mg) was saponified according to the procedure of Example 9 to yield crude product. Purification of the crude product is carried out by preparative thick-layer chromatography (silica gel plates, elution agent CHCl$_3$/MeOH-/acetone (4:3:3)) to yield 32 mg of Ru[(SO$_3$Na)$_2$batho]$_2$ [(SO$_3$Na)(SO$_2$NHCH$_2$CH$_2$COOH)bath]Cl$_2$.

EXAMPLE 18

Preparation of methyl p-[β-chloropropionyl]-5-phenylvalerate

In a stirring flask equipped with a reflux condenser are placed 9.3 g of AlCl$_3$, 10 ml of CS$_2$ and 1.98 ml of β-chloropropionyl chloride. To this mixture are added dropwise at room temperature within 5 minutes 3.61 g of 5-phenylvaleric acid (rinsing is carried out with 2 ml of CS$_2$). The reaction mixture is subsequently stirred for a further 15 minutes, warmed slightly and then cooled. The reaction mixture is then pipetted into a stirred mixture of ice, water and ether. The organic phase is washed neutral with bicarbonate solution and water. After drying over MgSO$_4$ the solvent is removed and 5.03 g of crystalline product are thus obtained.

EXAMPLE 19

Preparation of 5-[p-(7-phenyl-1,10-phenanthrolin-4-yl)phenyl]-pentanoic acid—[CH$_2$CH$_2$CH$_2$COOH)batho]

Under argon in a stirring flask are placed 2.54 g of 4-phenyl-8-aminoquinoline, 11.5 ml of H (85%) and 2.3 ml of arsenic acid solution (80% H$_3$AsO$_4$). The mixture is heated to 120° C. to dissolve the quinoline and thereafter 4.56 g of methyl P-[β-chloropropionyl]-5-phenylvalerate are added thereto within 5 minutes. The reaction mixture is suhsequently heated, while stirring within 10 minutes, to 140° C. and left at this temperature for a further 1 hour. The reaction mixture is then cooled and pipetted into a stirred mixture of 50 ml of water and 125 ml of CH$_2$Cl$_2$ which is cooled well with ice. The pH is brought to 5 by adding sodium hydroxide solution to pass the reaction product into the organic phase. After evaporation of the solvent there is obtained a crude product which contains a mixture of the methyl ester and free acid. By treatment with diazomethane (in ether/methanol) the mixture is completely converted into the methyl ester. After two-fold chromatography with ethyl acetate on Alox III (additionally deactivated with 1.5% $H_2O$) there are obtained 3.022 g of methyl ester. i.e. [($CH_2CH_2CH_2CH_2COOCH_3$)batho].

For the saponification, the methyl ester is dissolved in 20 ml of ethanol the solution is treated with sodium hydroxide solution (0.950 g of NaOH dissolved in 5 ml of $H_2O$) and heated to 80° C. under argon for 2 hours. The cooled solution is added to a $CH_2CL_2/H_2O$ mixture the pH of the solution is adjusted to 4–5 with 85% $H_3PO_4$ and the product is subsequently extracted with $CH_2Cl_2$. The concentrated $CH_2Cl_2$ extract is recrystallized from benzene to yield 1.35 g of product. A further 0.338 g of product is obtained from the concentrated mother liquor by recrystallization from ethanol to give a total yield of 1.688 g of [($CH_2CH_2CH_2COOH$)batho] m.p. 234°–235° C.

EXAMPLE 20

Preparation of the Ru complex
—Ru[$(SO_3Na)_2$batho]$_2$[($CH_2CH_2CH_2COOH$)batho]$Cl_2$

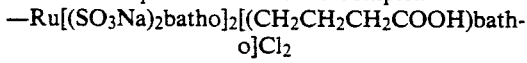

The compound of Example 19, i.e., 5-[p-(7-phenyl1.10-phenanthrolin-4-yl)- phenyl)-pentanoic acid (34.6mg) dissolved in 2 ml of methanol is added to a solution of 102.4 mg of Ru[$(SO_3Na)_2$batho]$_2Cl_2.2H_2O$ in 4 ml of methanol and 8 ml of water. This mixture is heated to reflux under $N_2$ for 3 hours, whereby an orange-red solution results. Thereafter, the solvent is removed by blowing in $N_2$. The purification of the crude product is carried out by means of preparative thick-layer chromatography. For this purpose, the complex is dissolved in a small amount of water and applied to 6 PSC plates ($SiO_2$ plates from Merck). After drying the plates at 70° chromatography is carried out with the elution agent chloroform/acetone/ methanol (4:3:3). The main zone product, extracted with water, was subjected a further 3 times to a preparative thick-layer chromatography, whereby the following elution agents were used: acetone/water (9:1). then acetone/water (8.5;1.5) and finally chloroform/methanol/water (50:50:2). For the removal of final traces of $SiO_2$, the extracted product was dissolved in a small amount of methanol and the undissolved silica gel was centrifuged off. The product was then precipitated from 1 ml of methanolic solution with 50 ml o acetone. Yield: 42.6 mg (red powder) identified as Ru[$(SO_3Na)_2$batho]$_2$[($CH_2CH_2Ch_2CH_2COOH$)batho]$Cl_2$.

EXAMPLE 21

Preparation of methyl p-[β-chloropropionyl]-6-phenylcaproate 17.2 g of $AlCl_3$, 18.5 ml of $CS_2$ and 3.6 ml of β-chloropropionyl chloride are placed in a stirring flask with a reflux condenser. 7.06 g of methyl 6-phenylcaproate are allowed to drop into this mixture at room temperature within 10 minutes (rinsing is carried out with 4 ml of $CS_2$). The reaction mixture is subsequently stirred for a further 15 minutes warmed slightly and then cooled. The reaction mixture is then pipetted into a stirred mixture of ice water and ether. The organic phase is washed neutral with bicarbonate solution and water. After drying over $MgSO_4$ the solvent is removed, 10.2 g of crystalline product identified as methyl p-[β-chloropropionyl]-6-phenyl-caproate are obtained.

EXAMPLE 22

Preparation of 6-(p-(7-phenyl-1,10-phenanthrolin-4-yl)-phenyl]-hexanoic acid—[($CH_2CH_2CH_2CH_2CH_2CH_2COOH$)bath]

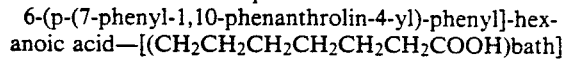

Under argon in a stirring flask is placed 5.90 g of 4-phenyl-8-aminoquinoline 27 ml of $H_3PO_4$ (85%) and 5.35 ml of arsenic acid solution (80% $H_3AsO_4$). The mixture is heated to 120° C. in order to d the quinoline. Thereafter 11.15 g of methyl p-[β-chloropropionyl]-6-phenylcaproate are added within 5 minutes. The reaction mixture is subsequently heated while stirring within 10 minutes to 140° C. and left at this temperature for a further 1 hour. For the working-up, the reaction mixture is cooled and pipetted into a stirred mixture of 100 ml of water and 250 ml of $CH_2Cl_2$ which is cooled well with ice. The pH is then brought to 5 by adding sodium hydroxide solution (about ⅜ of a solution of 45 g of NaOH in 200 ml of water). Thereby, the substance passes into the organic phase. After evaporation of the solvent there are obtained 15.76 g of a viscous oil which contains, besides the methyl ester, also free acid. By treatment with diazomethane (in ether/ methanol) the mixture is again converted completely into the methyl ester. This is chromatographed (fractions of 120 ml) with ethyl acetate on 350 g of Alox III (additionally deactivated with 1% $H_2O$); fractions 5 to 9 contain pure product.

Fractions 3, 4 and 10 are, on the other hand, still contaminated. They are again chromatographed (as previously described) with ethyl acetate over aluminium oxide. From the pure fractions of the two chromatographies there are obtained, after removing the solvent, 6.979 g of methyl ester, i.e., [($CH_2CH_2CH_2CH_2CH_2COOCH_3$) batho]. For the saponification, the methyl ester is dissolved in 45 ml of ethanol this solution is treated with sodium hydroxide solution (2.24 g of NaOH dissolved in 11 ml of $H_2O$) and heated to 80° C. under argon for 2 hours. The ethanol is then removed on a rotary evaporator and the residue is taken up in a mixture of $CH_2Cl_2$/water. The pH is adjusted to about 3 with 3.75 ml of $H_3PO_4$ 85% and the product is then extracted. The extract is washed neutral, dried and concentrated to 300 ml. After the addition of a total of 3.5 g of Norit SX-3 the solution is stirred for 40 minutes, filtered and concentrated to a small amount of $CH_2Cl_2$. 20 ml of benzene are added thereto and the crude product is left to crystallize out at room temperature for 48 hours. Purification of the crude product yielded [($CH_2CH_2CH_2CH_2CH_2COOH$)-batho]. m.p. 195° C.

EXAMPLE 23

Preparation of the Ru complex Ru[$(SO_3Na)_2$batho]$_2Cl_2.2H_2O$ [($CH_2CH_2CH_2CH_2Ch_2$-COOH)batho]$Cl_2$ To 134.2 mg of 6-[p-(7-phenyl-1,10-phenanthorlin-4-yl)-phenyl]hexanoic acid dissolved in 5.7 ml of methanol are added of 384 mg of Ru(($SO_3Na)_2$batho$_2Cl_2$2.$H_2O$ in 20 ml of methanol and 5 ml of water. This mixture is heated at reflux for 3 hours under $N_2$. whereby an orange-red solution results. The major part of the solvent is subsequently removed by blowing in $N_2$. The remainder is then removed completely with a rotary evaporator. The purification of the product is carried out firstly by two-fold column chromatography over SiO$_2$ with the elution agent chloroform/methanol/water (7:3:0.5). The complex is subsequently purified further by means of preparative thick-layer chromatography (SiO$_2$ plates from Merck). Elution agent: chloroform/methanol/water (7:3:0.5). After scratching-off the main zone is extracted with methanol to yield 162 mg of Ru[(SO$_3$Na)$_2$ batho]$_2$[(CH$_2$CH$_2$CH$_2$CH$_2$COOH)batho]Cl$_2$ as a red powder.

EXAMPLE 25

Preparation of benzobathophenanthrolinyl-pentanoic acid—[(CH$_2$CH$_2$CH$_2$CH$_2$COOH)benzobatho]

The synthesis of the title compound was carried out starting from 2-amino-3-napthoic acid by means of a Skraup's reaction analogously to the procedure described in Example 18. Total yield: 1.07 g.

EXAMPLE 25

Preparation of the Ru complex—Ru[(SO$_3$Na)$_2$batho]$_2$[(CH$_2$CH$_2$CH$_2$CH$_2$COOH)benzobatho]Cl$_2$ The Ru complex was prepared in an analogous manner to the procedure of Example 8 except that 1.28 g of Ru[(SO$_3$Na)$_2$batho]$_2$ Cl$_1$ and 0.561 g of [(CH$_2$CH$_2$CH$_2$COOH)benzobatho] was used. Yield: 1.1 g of a red powder.

EXAMPLE 26

Preparation of the Ru complex—Ru[(SO$_3$Na)$_2$batho]$_2$[(COOH)$_2$bpy]Cl$_2$

Following the procedure of Example 8, the title compound was prepared using 256 mg of Ru[(SO$_3$Na)$_2$batho]$_2$Cl$_2$, 49 mg of 4 4'-dicarboxy-2,2'-bipyridine and 60 mg of NaHCO$_3$ (for the solubilization of the bipyridine) in 35 ml of MeOH/H$_2$O (1:2). The reaction yielded 290 mg of a red powder identified as Ru[(SO$_3$Na)$_2$batho]$_2$[(COOH)$_2$ bpy)Cl$_2$

EXAMPLE 27

Labelling of anti-CEA with the Ru complex of Example 6

The coupling of the mixed Ru complex of Example 6 to anti-CEA was carried out with the aid of the water-soluble carbodiimide derivative N-cyclohexyl-N'-(2-morpholinoethyl)-carbodiimide-methyl-p-toluenesulphonate. As the complex has two reactive groups per molecule, double the molar amount of carbodiimide is used. The following stock solutions are prepared for the coupling reaction:
(1) 4.00 mg/ml of Ru complex of Example 6 in water at pH 4.5
(2) 2.17 mg/ml of anti-CEA from rabbit (DAKO Code No. A 115, Lot 112 B) in 200 mM NaHCO$_3$; pH 8.5.

"Stock Solution 1" (136 μl) is diluted with 264 μl of water pH 4.5 (adjusted with HCl). Thereafter 0.27 mg of N-cyclohexyl-N'-(2-morpholinoethyl)-carbodiimide-methyl-p-toluenesulphonate is added and the mixture mixed using a vortex mixer. After two minutes 400 ml of the anti-CEA "stock soluticn 2" are added thereto and the mixture is again mixed well in a vortex. The pH is adjusted to 8.5 by the addition of a small amount of 1N HCl, The reaction mixture is then left to stand at room temperature in the dark for 17 hours.

For the separation of the labelled anti-CEA, 500 ml of the reaction mixture wera chromatographed over a column (length 30 cm, diameter 9 mm) with acrylamide gel AcA-54 from LKB (elution agent: 150 mM NaCl, 10 mM Na phosphate. 0.02% NaN$_3$, pH 7.0). The fractions with the highest content of labelled anti-CEA were combined—a total of 5.2 ml. The content of anti-CEA and of Ru complex in this solution was determined by UV-spectroscopy (from the optical density at 278 nm—absorption of anti-CEA and Ru complex, as well as from the optical density at 445 nm—absorption of the Ru complex alone). The following concentrations were thus obtained:

$0.66 \times 10^{-6}$ M/l Ru complex
$(0.58 \times 10^{-6}$ M/l anti-CEA

This corresponds to a degree of labelling of 1.1.

EXAMPLE 28

Performance of a fluorescence immunoassay with CEA standards—sandwich test

For the quantitative determination of CEA-standards, a sandwich test was carried out as follows with a monoclonal CEA antibody and a polyclonal CEA antibody (labelled antibody from DAKO):

Into the requisite number of test tubes (10×75 mm) there are in each case pipetted 0.250 ml of CEA standard solution (0 ng/ml CEA; 2.5 ng/ml CEA: 5 ng/ml CEA; 10 ng/ml CEA and 20 ng/ml CEA in 150 mM NaCl, 10 mM Na phosphate with 20 g/l bovine serum albumin) in each case there is added a polystyrene bead (diameter 6.5 mm) sensitized with monoclonal anti-CEA and incubation is carried out at 37° C. for 24 hours. The polystyrene beads are subsequently washed three times with 2-5 ml of distilled water each time and then transferred into test tubes each of which contains 0.250 ml of buffer solution with $1 \times 10^{-8}$M/l labelled rabbit anti-CEA (degree of labelling 1.1).

After a 24 hours incubation at 37° C. the beads are again washed three times with 2-5 ml of distilled water each time and subsequently transferred into test tubes with in each case 2 ml of sulphuric acid (0.09N). After 30 minutes the sulphuric acid solution is pipetted into measurement cuvettes and the content of Ru complex is measured by fluorescence spectroscopy (excitation wavelength 453 nm. emission wavelength 612 nm).

The measurement was carried out with the apparatus described earlier using an edge filter B 610 from Balzers, a periodic delay of the fluorescence measurement of 2 usec (based on the excitation pulse) and an opening of the measurement aperture of 3 μsec.

In Table I there are given the values of a CEA determination which was carried out with a series of CEA standards.

The sensitivity in the case of this two-step test amounts to 60 pg/ml CEA.

TABLE I

| Determination by fluorescence spectroscopy of CEA standards (two-step procedure) | |
|---|---|
| Concentration of CEA | Rel. fluorescence intensity |
| 0 ng/ml CEA | 0.071 |
| 2.5 ng/ml CEA | 0.532 |
| 5 ng/ml CEA | 1.041 |
| 10 ng/ml CEA | 1.846 |
| 20 ng/ml CEA | 4.121 |

EXAMPLE 29

Performance of a fluorescense immuno assay with CEA standards - one - pot procedure The CEA test can also be carried out in a one-pot procedure in accordance with the following method.

To the requisite number of test tubes (10×75 mm) there are in each case added 0.125 ml of CEA standard solution (0 ng/ml CEA; 2.5 ng/ml CEA; 5 ng/ml CEA; 10 ng/ml CEA; 20 ng/ml CEA in foetal calf serum) as well as in each case 0.125 ml of a solution with $2 \times 10^{-8}$ M/l rabbit anti-CEA which is labelled with the Ru complex (degree of labelling 1.25; dilution buffer pH 7.1 containing 0.1 M/l Tris, 20% foetal calf serum 0.05% Thimerosal and 0.02% Tween 20). Then, in each case there is added thereto a polystyrene bead (diameter 6.5 mm sensitized with monoclonal anti-CEA) and incubation is carried out at 37° C. for 24 hours. The beads are subsequently washed three times with 2 to 5 ml of distilled water each time and then transferred into test tubes with in each case 2 ml of sulphuric acid (o.09N). After 30 minutes the sulphuric acid solution is pipetted into measurement cuvettes and the content of Ru complex is measured by fluorescence spectroscopy (the measurement conditions are identical with those of Example 28. The results of this CEA determination are compiled in Table II. A sensitivity of 430 pg/ml CEA is found in the one-pot procedure.

TABLE II

| Concentration of CEA (Roche standard solutions) | Rel. fluorescence intensity |
| --- | --- |
| 0 ng/ml CEA | 0.27 |
| 2.5 ng/ml CEA | 1.21 |
| 5 ng/ml CEA | 2.66 |
| 10 ng/ml CEA | 5.13 |
| 20 ng/ml CEA | 9.74 |

EXAMPLE 30

Labelling of anti-HCG

The labelling of anti-HCG with the Ru complex of Example 6 was carried out in the same manner as that of anti-CEA in accordance with Example 27. The following stock solutions were prepared for the coupling reaction:

(1) 4.00 mg/ml of Ru complex of Example 6 in water at pH 4.5

(2) 10.83 mg/ml of anti-HCG from rabbit (DAKO Code No. A 231 Lot 032 A) in 200 mM NaHCO$_3$; pH 8.5.

"Stock Solution 1" (150 ml) is diluted with 250 ml of water pH 4.5 (adjusted with HCl). Thereafter, 0.30 mg of N-cyclohexyl-N'-(2-morpholinoethyl)-carbodiimidemethyl-p-toluenesulphonate is added to this solution and the mixture is mixed using a vortex. mixer. After minutes there is added thereto the anti-HCG solution (222 ml of stock solution 2 diluted with 178 μl of a 200 mM NaHCO$_2$ solution pH 8.5) and the mixture is mixed well in a vortex. The pH-value is adjusted to 8.5 with a small amount of HCl. The reaction mixture is then left to stand at room temperature in the dark for 17 hours. For the separation of the labelled anti-HCG, 500 ml of the reaction mixture are chromatographed over a column (length 30 cm diameter 9 mm) with acrylamide gel AcA-54 (from LKB) (elution agent 150 mM NaCl, 10 mM Na phosphate 0.02% NaN$_3$. pH 7.0). The fractions with the highest content of labelled anti-HCG are combined—a total of 5.2 ml. The content of anti-HCG and of Ru complex is determined in this solution by UV-spectroscopy. The following concentrations are thus obtained:

$2.01 \times 10^{-6}$ M/l Ru complex
$2.04 \times 10^{-6}$ M/l anti-HCG

This corresponds to a degree of labelling of 1.0.

EXAMPLE 31

Performance of a fluorescence immunoassay with β-HCG standards

For the quantitative determination of 8-HCG standards, a sandwich test was carried out as follows with a monoclonal β-HCG antibody and a polyclonal HCG antibody (labelled antibody from DAKO). To the requisite number of test tubes (10×75 mm) there are added 0.050 ml of β-HCG standard solution (0 mIU/ml; 10 mIU/ml; 25 mIU/ml; 50 mIU/ml; 100 mIU/ml; 200 mIU/ml). Thereafter 0.050 ml of a solution containing $5.12 \times 10^{-8}$ M/l anti-HCG which is labelled as described in Example 30 in dilution buffer pH 7.1 (0.1 M/l Tris. 20%. foetal calf serum 0.05% Thimerosal and 0.02% Tween 20). An additional 0.150 ml of buffer solution (150 mM NaCl, 10 mm Na phosphate with 20 g/l bovine serum albumin) is added to each test tube and finally a polystyrene bead (diameter 6.5 mm sensitized with monoclonal anti-β-HCG) is added to each tube and incubation is carried out at 37° C. for 16 hours. The beads are subsequently washed three times with 2 to 5 ml of distilled water each time and then transferred into test tubes with in 2 ml of sulphuric acid (0.09N). After 30 minutes the sulphuric acid solution is pipetted into measurement cuvettes and the content of Ru complex is measured by fluorescence spectroscopy as described in Example 28. The results of the β-HCG determination are summarized in Table III. A sensitivity of 2.2 mIU/ml β-HCG is found.

TABLE III

Determination by fluorescence spectroscopy of β-HCG standards (one-pot procedure)

| Concentration of β-HCG | Rel. fluorescence intensity |
| --- | --- |
| 0 mIU/ml | 0.44 |
| 10 mIU/ml | 0.34 |
| 25 mIU/ml | 0.80 |
| 50 mIU/ml | 1.56 |
| 100 mIU/ml | 2.78 |
| 200 mIU/ml | 5.81 |

EXAMPLE 32

Labelling of anti-a-interferon

The labelling of monoclonal anit-a-inferferon (from Roche Diagnostica) with the Ru complex of Example 6 was carried out in the same manner as that of anti-CEA in accordance with Example 27. The following stock solutions were prepared for the coupling reaction:

(1) 3.75 mg of Ru complex of Example 6 in water at pH 4.5.

(2) 6.0 mg/ml of monoclonal anti-a-interferon in 200 mM NaHCO$_3$; pH 8.5.

A water-soluble carbodiimide derivative (0.81 mg) is added to 400 μl of "Stock Solution 1" and mixed for a short time in a vortex. After 2 minutes there are added thereto 400 μl of the anti-a-interferon Stock Solution 2 and the mixture is mixed using a vortex mixer. The reaction mixture is then left to stand at room temperature in the dark for 17 hours. For the separation of the labelled anti-a-interferon, 500 ml of the reaction mixture are chromatographed over a column (length 30 cm, diameter 9 mm) with acrylamide gel AcA-54 from LKB (elution agent: 150 mM NaCl, 10 mM Na phosphate, 0.02% NaN$_3$, pH 7.0). The fractions with the highest content of labelled anti-a-interferon are combined—a total of 5.2 ml. The content of anti-a-interferon and of Ru complex of Example 6 is determined in by UV-spectroscopy. The following concentrations are obtained:

$11.5 \times 10^{-6}$ M/l Ru complex $1.8 \times 10^{-6}$ M/l an.i-a-interferon (monoclonal). This corresponds to a degree of labelling of 6.4.

EXAMPLE 33

Performance of a fluorescence immunoassay with a-interferon standards

For the quantitative determination of interferon-raA standards (recombinant leucocyte interferon), there is used a sandwich test developed by Roche Diagnostica as a EIA. In place of the enzyme-labelled second antibody there is. however, used monoclonal anti-interferon which is labelled with the Ru complex of Example 6 (degree of labelling 6.4).

The quantitative determination of the various interferon-raA standards was carried out according to the following procedure (one-step test).

To the requisite number of test tubes ($10 \times 75$ mm) there are in each case added 0.100 ml of interferon-raA standard solution (0 U/ml r IFNaA; 25 U/ml r IFNaA; 50 U/ml r IFNaA; 100 U/ml r IFNaA: 150 U/ml r IFNaA: 200 U/ml r IFNaA in normal human serum with Thimerosal) as well as in each case 0.50 ml of a solution with $5.26 \times 10^{-10}$ M/l monoclonal anti-a-interferon which is labelled with the Ru complex of Example 6 buffer system: 150 mM NaCl. 10 mM Na phosphate pH 7.5).There is then added thereto in each case a polystyrene bead (diameter 6.5 mm; sensitized with monoclonal anti-interferon) and incubation is carried out at room temperature (26° C.) for 24 hours. The beads are subsequently washed three times with 2–5 ml of distilled water each time and then transferred into test tubes with in each case 2 ml of sulphuric acid (0.09N). After 30 minutes the sulphuric acid solution is pipetted into measurement cuvettes and the content of Ru complex is measured by fluorescence spectroscopy (The measurement conditions are identical with those of Example 28). The results of the r IFNaA determinations which are summarized in Table IV illustrate that in the range of 0–200 U/ml there is an approximately linear relationship between the fluorescence intensity and the r IFN$^\alpha$A concentration. The sensitivity amounts to 0.46 U/ml r IFNaA.

TABLE IV

| Determination by fluorescence spectroscopy of r IFNaA standards | |
|---|---|
| Concentration of r IFNaA (Roche standard solutions) | Rel. fluorescence intensity |
| 0 U/ml | 0.14 |
| 25 U/ml | 0.51 |
| 50 U/ml | 0.89 |
| 100 U/ml | 1.80 |
| 150 U/ml | 2.77 |
| 200 U/ml | 4.01 |

EXAMPLE 34

Labelling of polyclonal anti-HCG with the Ru complex of Example 20

The following stock solutions are prepared for the coupling reaction:
(1) 5.4 mg/ml of Ru complex of Example 20 in water at pH 4.5.
(2) 6.0 mg/ml of polyclonal anti-HCG from rabbits (DAKO Code No. A 231. Lot 032A) in 200 mM NaHCO$_3$; pH 8.5.

The coupling reaction is carried out according to the procedure described in Example 27. For this purpose there are used in each case 400 µl of the Stock Solutions 1 and 2 as well as 0.56 mg of water-soluble carbodiimide. The labelled antibodies were separated from excess Ru complex by gel chromatography as described in Example 32. The UV-spectroscopic determination of the content of anti-HCG and of Ru complex gave the following values:

$3.81 \times 10^{-6}$ M/l Ru complex $1.87 \times 10^{-6}$ M/l anti-HCH (polyclonal).

This corresponds to a degree of labelling of 2.0.

EXAMPLE 35

Labelling of polyclonal anti-CEA with the Ru complex of Example 23

The following stock solutions are prepared for the coupling reaction:
(1) 1.71 mg/ml of Ru complex of Example 23 in water at pH 4.5.
(2) 2.17 mg/ml of polyclonal anti-CEA from rabbits (DAKO Code No. A115. Lot 112B) in 200 mM NaHCO$_3$ pH 8.5.

The coupling reaction is carried out according to the procedure described in Example 27. For this purpose there are used in each case 400 µl of the stock solutions 1 and 2 as well as 0.19 mg of water-soluble carbodiimide. The labelled antibodies were separated from excess Ru complex by gel chromatography as described in Example 27. The UV-spectroscopic determination of the content of anti-CEA and of Ru complex gave the following values;

$0.43 \times 10^{-6}$ M/l Ru complex $0.94 \times 10^{-6}$ M/l anti-CEA

This corresponds to a degree of labelling of 0.5.

EXAMPLE 36

Labelling of h-IgC with the Ru complex of Example 17

The following stock solutions are prepared for the coupling reaction:
(1) 3.6 mg/ml of Ru complex of Example 17 in water at pH 4.5.
2) 6.0 mg/ml of h-IgG in 200 mM NaHCO ; pH 8.5.

The coupling reaction is carried out according to the procedure described in Example 27. There are used thereby in each case 400 µl of the stock solutions 1 and 2 as well as 0.37 mg of water-soluble carbodiimide. The labelled antibodies are separated from excess Ru complex by gel chromatography as described in Example 27. The UV-spectroscopic determination of the content of h-IgG and of Ru complex gave the following values:

$2.31 \times 10^{-6}$ M/l Ru complex $1.62 \times 10^{-6}$ M/l h-IgG

This corresponds to a degree of labelling of 1.4.

EXAMPLE 37

Labelling of h-IgG with the Ru complex of Example 3

The following stock solutions are prepared for the coupling reaction;
(1) 4.0 mg/ml of Ru complex of Example 3 in water at pH 4.5
(2) 6.0 mg/ml of h-IgG in 200 mM $NaHCO_3$; pH 8.5.

The coupling reaction is carried out according to the procedure described in Example 27. There are thereby used in each case 400 µl of the stock solutions 1 and 2 as well as 1.11 mg of water-soluble carbodiimide. The labelled antibodies are separated from excess Ru complex by gel chromatography as described in Example 22. The UV-spectroscopic determination of the content of H-IgG and of Ru complex gave the following values;
10.4×$10^{-6}$ M/l Ru complex
1.8×$10^{-6}$ M/l h-IgG
This corresponds to a degree of labelling of 5.8.

EXAMPLE 38

Labelling of h-IgG with the Ru complex of Example 26

The following stock solutions are prepared for the coupling reaction:
(1) 29 0 mg/ml of Ru complex of Example 26 in water at pH 4.5.
(2) 6.0 mg/ml of h-IgG in 200 mM $NaHCO_4$ pH 8.5.

The coupling reaction is carried out according to the procedure described in Example 27. There are thereby used 526 µl of the stock solution 1 and 400 µl of the stock solution 2 as well as 7.45 mg of water-soluble carbodiimide. The labelled antibodies are separated from excess Ru complex by gel chromatography as described in Example 22 The UV-spectroscopic determination of the content of h-IgG and of Ru complex gave the following values;
0.81×$10^{-6}$ M/l Ru complex
0.78×$10^{-6}$ M/l h-IgG
This corresponds to a degree of labelling of 1.0.

EXAMPLE 39

Labelling of b-IgG with the Ru comolex of Example 9

The following stock solutions are prepared for the coupling reaction:
(1) 3.7 mg/ml of Ru complex of Example 9 in water at pH 4.5.
(2) 6.0 mg/ml of h-IgG in 200 mM $NaHCO_3$; pH 8.5.
The coupling reaction is carried out according to procedure described in Example 27. There are thereby used in each case 400 µl of the stock solutions 1 and 2 as well as 0.75 mg of water-soluble carbodiimide. The labelled antibodies are separated from excess Ru complex by gel chromatography as described in Example 27. The UV-spectroscopic determination of the content of h-IgG and of Ru complex gave the following values:
4.41×$10^{-6}$ M/l Ru complex
1.2×$10^{-6}$ M/I h-IgG
This corresponds to a degree of labelling of 3.6.

EXAMPLE 40

Labelling of h-IgG with the Ru complex of Example 12

The following stock solutions are prepared for the coupling reaction:
(1) 3.81 mg/ml of Ru complex of Example 12 in water at pH 4.5.
(2) 6.0 mg/ml of h-IgG in 200 mM $NaHCO_3$; pH 8.5.

The coupling reaction is carried out according to the procedure described in Example 27. There are thereby used in each case 400 µl of the stock solutions 1 and 2 as well as 0.75 mg of water-soluble carbodiimide. The labelled antibodies are separated from excess Ru complex by gel chromatography as described in Example 27. The UV-spectroscopic determination of the content of h-IgG and of Ru complex gave the following values:
5.5×$10^{-6}$ M/l Ru complex
1 17×$10^{-6}$ M/l h-IgG
This corresponds to a degree of labelling of 4.70.

EXAMPLE 41

Labelling of h-IgG with the Ru complex of Example 15

The following stock solutions are prepared for the coupling reaction;
(1) 3.87 mg/ml of Ru complex of Example 15 in water at pH 4.5.
(2) 6.0 mg/ml of h-IgG in 200 mM $NaHCO_3$; pH 8.5.
The coupling reaction is carried out according to the procedure described in Example 27. There are thereby used in each case 400 µl of the stock solutions 1 and 2 as well as 0.75 mg of water-soluble carbodiimide.

The labelled antibodies are separated from excess Ru complex by gel chromatography as described in Example 27. The UV-spectroscopic determination of the content of h-IgG and of Ru complex gave the following values:
11.7×$10^{-6}$ M/l Ru complex
1 04×$10^{-6}$ M/l h-IgG
This corresponds to a degree of labelling of 11.2 .

EXAMPLE 42

Labelling of h-IgG with the Ru complex of Example 25

The following stock solutions are prepared for the coupling reaction:
(1) 3.45 mg/ml of Ru complex of Example 25 in water at pH 4.5.
(2) 6.0 mg/ml of h-IgG in 200 mM $NaHCO_3$; pH 8.5.
The coupling reaction is carried out according to the procedure described in Example 27. There are thereby used in each case 400 µl of the stock solutions 1 and 2 as well as 0.375 mg of water-soluble carbodiimide. The labelled antibodies are separated from excess Ru complex by gel chromatography as described in Example 27. The UV-spectroscopic determination of the content of h-IgG and of Ru complex gave the following values:
5.69×$10^{-6}$ M/l Ru complex
0.45×$10^{-6}$ M/l h-IgC
This corresponds to a degree of labelling of 12.8.

What is claimed is:

1. A ruthenium complex of the general formula $$Ru^2L_1L_2L_3$$

wherein $L_1$ and $L_2$ are the same or different and are bathophenanthroline or benzobathophenanthroline groups substituted with sulphonic acid groups as groups conferring water solubility, and wherein $L_2$ is a member of the group consisting of a bathophenanthorline group and a benzobathophenanthroline group, both of which are substituted with a moiety of the formula:

$$-X_{13}(CH_2)_n-Y$$

wherein —X— is selected from the group consisting of —SO$_2$—NH—, —S—, —O—, —COO—, —CO—NH—, and a single bond; n=1–8; and Y is selected from the group consisting of COOH, NH$_2$, NCS, I and SO$_2$Hal group.

2. A ruthenium complex according to claim 1, wherein the ligand L$_3$ is substituted with the group SO$_2$—NH—(CH$_2$)$_n$COOH in which n is a whole number of from 1–5.

3. A ruthernium complex according to claim 1, wherein the ligand L$_3$ is substituted with the group —(CH$_2$)$_4$—COOH.

4. A ruthenium complex according to claim 1, wherein the ligand L$_3$ is substituted with the grou —(CH$_2$)$_5$—COOH.

* * * * *

UNITED STATES PATENT AND TRADEMARK OFFICE
CERTIFICATE OF CORRECTION

PATENT NO. : 5,075,447

DATED : December 24, 1991

INVENTOR(S) : Francis Muller and Dieter Schmidt

It is certified that error appears in the above—identified patent and that said Letters Patent is hereby corrected as shown below:

In claim 1, column 26, line 57, please delete "$Ru^{2} L_1 L_2 L_3$" and insert therefor -- $Ru^{2+} L_1 L_2 L_3 I$ --;

In claim 1, column 26, line 62, please delete "$L_2$" and insert therefor -- $L_3$ --;

In claim 1, column 26, line 63, please delete "bathophenanthorline" and insert therefor -- bathophenanthroline --;

In claim 1, column 26, line 67, please delete the structure and insert therefor -- $-X-(CH_2)_n-Y$ --;

In claim 3, column 28, line 3, delete "ruthernium" and insert therefor -- ruthenium --;

In claim 4, column 28, line 7, delete "grou" and insert therefor -- group --.

UNITED STATES PATENT AND TRADEMARK OFFICE
CERTIFICATE OF CORRECTION

PATENT NO. : 5,075,447
DATED      : December 24, 1991
INVENTOR(S) : Francis Muller et al.

It is certified that error appears in the above-identified patent and that said Letters Patent is hereby corrected as shown below:

Claim 4, column 28, line 7, delete "grou" and insert --group--.

Signed and Sealed this

Thirteenth Day of April, 1993

Attest:

STEPHEN G. KUNIN

*Attesting Officer*    *Acting Commissioner of Patents and Trademarks*